United States Patent [19]

Mayer et al.

[11] 4,301,186

[45] Nov. 17, 1981

[54] AMMONIUM SALTS OF α-KETOCARBOXYLIC ACIDS

[75] Inventors: Wolfram Mayer; Hans Rudolph, both of Krefeld; Eckhard De Cleur, Duisburg; Manfred Schönfelder, Leverkusen, all of Fed. Rep. of Germany

[73] Assignee: Bayer Aktiengesellschaft, Leverkusen, Fed. Rep. of Germany

[21] Appl. No.: 53,009

[22] Filed: Jun. 28, 1979

[30] Foreign Application Priority Data

Jul. 14, 1978 [DE] Fed. Rep. of Germany ....... 2830954

[51] Int. Cl.$^3$ .............................................. B05D 3/06
[52] U.S. Cl. .............................. 427/54.1; 204/159.15; 204/159.19; 260/346.22; 260/347.3; 260/465 D; 260/465.4; 260/501.1; 260/501.17; 260/501.18; 260/501.20; 525/454; 525/526; 525/529; 526/317; 528/44; 528/49; 528/75; 528/113; 528/114; 528/205; 544/107; 544/402; 546/168; 546/314; 546/315; 548/325; 548/335; 549/70; 560/51; 560/52; 560/53; 560/54; 560/176; 560/183; 562/431; 562/433; 562/435; 562/442; 562/443; 562/464; 562/493; 562/495; 562/567; 562/568; 562/574; 562/577; 562/578 562/597; 562/598

[58] Field of Search ........... 260/501.1, 501.17, 501.18, 260/501.2, 32.8 EP, 33.2 EP, 33.6 EP, 31.4 EP; 562/433, 442, 443, 459, 460, 461, 462, 431, 435, 598, 495, 464, 577, 578, 493, 568, 567, 601, 574, 597, 504, 509, 508; 560/51, 52, 53, 176, 54, 183; 526/317; 525/454, 526, 529; 528/49, 44, 75, 113, 114, 205; 204/159.14, 159.15, 159.19, 159.22, 159.23, 159.24; 427/54.1, 386, 385.5, 388.1, 388.2, 421, 389, 389.9, 391, 384, 430.1, 393.6, 389.7, 435, 428; 546/168, 314, 315; 544/402, 107; 548/335, 325; 549/70

[56] References Cited

U.S. PATENT DOCUMENTS 3,306,856  2/1967  Hu ..................................... 560/51 X

FOREIGN PATENT DOCUMENTS 1455695  11/1976  United Kingdom .

OTHER PUBLICATIONS

Chemisches Zentralblatt, Mar.–Apr., 1937, pp. 2145–2146.

Houben–Weyl Method der Organischen Chemie, vol. XI, No. 1, pp. 961–963.

Primary Examiner—Michael R. Lusignan
Assistant Examiner—Thurman K. Page
Attorney, Agent, or Firm—Gene Harsh; Lawrence S. Pope; Thomas W. Roy

[57] ABSTRACT

This invention relates to new ammonium salts of α-ketocarboxylic acids, to their use for the production of amines in situ by photochemical decomposition and to photochemically hardenable coating compositions containing these ammonium salts.

12 Claims, No Drawings

AMMONIUM SALTS OF α-KETOCARBOXYLIC ACIDS

BACKGROUND OF THE INVENTION

By virtue of their very wide range of chemical and physical properties, monoamines and polyamines are used as reactants in a variety of different chemical reactions. Reference is merely made here to their catalytic activity in numerous chemical reactions attributable to their basicity and to their use as crosslinking agents for polyurethane and epoxide resins. For many applications, it is desirable not to use the free amines, but instead to add the amines to the reaction mixture in a masked form from which they are released at a specific time to initiate the required reaction.

It is possible, for example, to release amines from enamines, ketimines and aldimines by the addition of water. Unfortunately, one disadvantage of these compounds lies in their high sensitivity to moisture; tertiary amine nitrogen atoms cannot be blocked in this way. It is also known that amines can be released from quaternary ammonium salts by heating to above 100° C. (Houben-Weyl, Methoden der Organischen Chemie, Vol. XI, 1). In many cases, however, it is desired to release the amines at considerably lower temperatures.

It has now surprisingly been found that amines can be released from ammonium salts of β,γ-unsaturated α-ketocarboxylic acids, even at room temperature, under the action of UV-light having a wavelength in the range of from 250 to 500 nm, the ketocarboxylic acid undergoing decarboxylation.

SUMMARY OF THE INVENTION

Accordingly, the present invention relates to ammonium salts of α-ketocarboxylic acids corresponding to the following general formula:

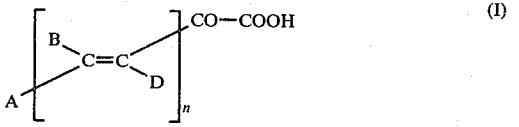

(I)

wherein
n represents an integer of from about 1 to 4, preferably about 1 or 2 and, with particular preference 1,
A and B are the same or different and represent hydrogen, and optionally branched and/or halogen- or methoxy-substituted alkyl radical containing from about 1 to 10, preferably from about 1 to 4 carbon atoms, a cycloalkyl radical containing from about 5 to 15, preferably from about 6 to 10 carbon atoms, an aryl radical containing from about 6 to 15, preferably from about 6 to 10 carbon atoms which may optionally be substituted by —OH, —R, —OR, —SR, halogen, —NO$_2$, —COR, —COOH, —CN, —COOR, —CONH$_2$, —OR', —SR' or —COR', a C$_{4-10}$ and preferably a C$_{5-9}$-heterocyclic radical containing oxygen, sulphur and/or nitrogen as a hetero atom, or A and B together represent a 5-membered or 6-membered cycloaliphatic ring optionally containing oxygen or nitrogen as a hetero atom, and
D represents hydrogen, halogen, —OH, —COOH, —COOR, —CN, —OR, —COR, —COR', —CCl$_3$, an optionally branched alkyl radical containing from about 1 to 10, preferably from about 1 to 4 carbon atoms, a cycloalkyl radical containing from about 5 to 15, preferably from about 6 to 10 carbon atoms, an aryl radical containing from about 6 to 15, preferably from about 6 to 10 carbon atoms which may optionally be substituted by —OH, —R, —OR, —SR, halogen, —NO$_2$, —COR, —COOH, —CN, —COOR, —CONH$_2$, —OR', —SR' or —COR' or a C$_{4-10}$ and preferably a C$_{5-9}$-heterocyclic radical containing oxygen and/or nitrogen as a hetero atom,
wherein
R represents an optionally halogen substituted alkyl group containing from about 1 to 6 carbon atoms, preferably methyl, ethyl or tert.-butyl and
R' represents an aryl group containing from about 6 to 12 carbon atoms, preferably phenyl.

Preferably, either A or B represents hydrogen, particularly when n>1. In another preferred embodiment, either A or B represents an aromatic radical such as is defined above and, with particular preference, a phenyl radical optionally substituted by chlorine, a methyl, methoxy or nitro group.

D preferably represents a halogen atom, a methyl radical, an acetyl radical or a phenyl radical optionally substituted by a methyl, methoxy or nitro group or by a chlorine atom or, with particular preference, represents hydrogen (particularly when n>1).

With particular preference, either A or B represents a methyl- or chlorine substituted phenyl radical, in which case A or B alternatively represents hydrogen.

The present invention also relates to a process for releasing an amine from its blocked form, characterized in that the salt of the amine with an α-ketocarboxylic acid corresponding to general formula I above is irradiated with light having a wavelength in the range of from about 250 to 500 nm.

The present invention also relates to coating compositions based on polyurethane or epoxide resin precursors hardening in the presence of amines, characterized in that they contain from about 0.1 to 40% by weight, preferably from about 0.3 to 15% by weight, of the ammonium salts described above.

DETAILED DESCRIPTION OF THE INVENTION

Examples of unsaturated α-ketocarboxylic acids according to the instant invention are ethylidene pyruvic acid, benzylidene pyruvic acid, p-methyl benzylidene pyruvic acid, o-chlorobenzylidene pyruvic acid, p-methoxy benzylidene pyruvic acid, cyclohexylidene pyruvic acid, furfurylidene pyruvic acid, 4-ethoxy-2-oxobutene-3-carboxylic acid, 3-benzoyl-2-oxobutene-3-carboxylic acid, 4-aniline-2-oxo-4-phenyl-butene-3-carboxylic acid, 4-formyl-2-oxobutene-3-carboxylic acid, 4-pyridine-2-oxobutene-3-carboxylic acid, 4,4-diphenyl-2-oxobutene-3-carboxylic acid and 4-thiophene-2-oxobutene-3-carboxylic acid.

In addition to ammonia, suitable amine components for the ammonium salts according to the present invention are any compounds containing one or more primary and/or secondary and/or tertiary (preferably tertiary) amine nitrogen atoms and having a molecular weight of from about 31 to 500, preferably from about 100 to 300. These compounds preferably contain from about 1 to 5 amine nitrogen atoms and, with particular preference, from about 1 to 3 amine nitrogen atoms and, in addition, may contain other functional groups, such as hydroxyl, mercapto, ether, thioether, amide and ester groups or even halogen atoms.

Examples of amines suitable for use in accordance with the present invention are methylamine, dimethylamine, ethylamine, diethylamine, ethanolamine, diethanolamine, tertiary amines, such as triethylamine, tributylamine, N-methyl morpholine, N-ethyl morpholine, N,N,N',N'-tetramethyl ethylene diamine, pentamethyl diethylene triamine and higher homologs (German Offenlegungsschrift Nos. 2,624,527 and 2,624,528), 1,4-diazabicyclo-[2,2,2]octane, N-methyl-N'-dimethylaminoethyl piperazine, bis-(dimethylamine-alkyl)-piperazines (German Offenlegungsschrift No. 2,636,787), N,N-dimethyl benzylamine, N,N-dimethyl cyclohexylamine, N,N-diethyl benzylamine, bis-(N,N-diethylaminoethyl)-adipate, N,N,N'N'-tetramethyl-1,3-butane diamine, N,N-dimethyl-$\beta$-phenylethylamine, 1,2-dimethyl imidazole, 2-methyl imidazole, monocyclic and bicyclic amidines (German Offenlegungsschrift No. 1,720,633), bis-(dialkylamino)-alkyl ethers (U.S. Pat. No. 3,330,782, German Auslegeschrift No. 1,030,558, German Offenlegungschrift Nos. 1,804,361 and 2,618,280) and tertiary amines containing amide groups (preferably formamide groups) according to German Offenlegungsschrift No. 2,523,633 and 2,732,929); tertiary amines containing active hydrogen atoms, for example triethanolamine, triisopropanolamine, N-methyl diethanolamine, N-ethyl diethanolamine, N,N-dimethylethanolamine, their reaction products with alkylene oxides, such as propylene oxide and/or ethylene oxide, also secondary-tertiary amines according to German Offenlegungsschrift No. 2,732,292; silaamines containing carbon-silicone bonds of the type described, for example, in German Pat. No. 1,229,290 (corresponding to U.S. Pat. 3,620,984), for example 2,2,4-trimethyl-2-silamorpholine and 1,3-diethylaminomethyl tetramethyl disiloxane.

Primary aliphatic diamines suitable for use in accordance with the present invention are, for example, ethylene diamine, 1,4-tetramethylene diamine, 1,11-undecamethylene diamine, 1,12-dodecamethylene diamine and mixtures thereof, 1-amino-3,3,5-trimethyl-5-aminomethyl cyclohexane ("isophorone diamine"), 2,4- and 2,6-hexahydrotolylene diamine and mixtures thereof, perhydro-2,4'- and 4,4-diaminodiphenyl methane, p-xylene diamine, bis-(3-aminopropyl)-methylamine, diaminoperhydro anthracenes (German Offenlegungsschrift No. 2,638,731) and cycloaliphatic triamines according to to German Offenlegungsschrift No. 2,614,244. It is also possible in accordance with the present invention to use hydrazine and substituted hydrazines, for example methyl hydrazine, N,N'-dimethyl hydrazine and their homologs, also acid dihydrazides, for example carbodihydrazide, oxalic acid dihydrazide, the dihydrazides of malonic acid, succinic acid, glutaric acid, adipic acid, $\beta$-methyl adipic acid, sebacic acid, hydracrylic acid and terephthalic acid; semicarbazido alkylene hydrazides such as $\beta$-semicarbazido propionic acid hydrazide (German Offenlegungsschrift No. 1,770,591), semicarbazido alkylene carbazinic esters such as 2-semicarbazidoethyl carbazinic ester (German Offenlegungsschrift No. 1,918,504) or even amino semicarbazide compounds such as $\beta$-aminoethyl semicarbazido carbonate (German Offenlegungsschrift No. 1,902,931).

Examples of primary aromatic diamines are bisanthranilic acid esters according to German Offenlegungsschrift Nos. 2,040,644 and 2,160,590, 3,5- and 2,4-diaminobenzoic acid esters according to German Offenlegungsschrift No. 2,025,900, the diamines containing ester groups described in German Offenlegungsschrift Nos. 1,803,635 (U.S. Pat. Nos. 3,681,290 and 3,736,350), 2,040,650 and 2,160,589, the diamines containing ether groups according to German Offenlegungsschrift Nos. 1,770,525 and 1,809,172 (U.S. Pat. Nos. 3,654,364 and 3,736,295), 2-halogen-1,3-phenylene diamines optionally substituted in the 5-position (German Offenlegungsschrift Nos. 2,001,772; 2,025,896 and 2,065,869), 3,3'-dichloro-4,4'-diaminodiphenyl methane, tolylene diamine, 4,4'-diaminodiphenyl methane, 4,4'-diaminodiphenyl disulphides (German Offenlegungsschrift No. 2,404,976), diaminodiphenyl dithioethers (German Offenlegungsschrift No. 2,509,404), aromatic diamines substituted by alkyl thio groups (German Offenlegungsschrift No. 2,638,760), diaminobenzene phosphonic acid esters (German Offenlegungsschrift No. 2,459,491), aromatic diamines containing sulphonates or carboxylate groups (German Offenlegungsschrift No. 2,720,166) and the high-melting diamines according to German Offenlegungsschrift No. 2,635,400. Examples of aliphatic-aromatic diamines are the aminoalkyl thioanilines according to German Offenlegungsschrift No. 2,734,574.

Monoamines suitable for use in accordance with the present invention are 1-mercapto-3-aminopropane, butyl and dibutylamine, octylamine, stearylamine, N-methyl stearylamine, pyrrolidine, piperidine and cyclohexylamine, Amines preferably used in accordance with the present invention are diethylamine, triethylamine, diethanolamine, triethylamine, tributylamine, N,N-dimethyl benzylamine, diazabicycloundecene (DBU), diazabicyclo-octane (DABCO) and dibutylamine.

The $\alpha$-ketocarboxylic acids corresponding to formula I on which the ammonium salts according to the present invention are based are largely known from the literature. They may be obtained by methods known per se, for example, by condensing a pyruvic acid corresponding to the following general formula:

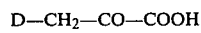

D—CH$_2$—CO—COOH with an aldehyde or ketone corresponding to the following general formula:

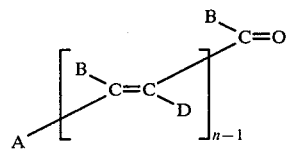

wherein A, B, D and n are defined as above.

This reaction gives particularly good yields when A or B represent an aromatic radical.

Another synthesis route uses as its starting component an unsaturated aldehyde corresponding to the following general formula:

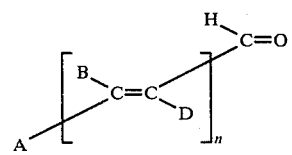

which is converted into the cyanhydrin by reaction with HCN. The cyanhydrin is oxidized to form the α-ketonitrile which is, in turn, hydrolyzed to form the α-ketocarboxylic acid.

The ammonium salts according to the present invention are generally crystalline compounds having a defined melting point. They are soluble in numerous organic solvents, for example, acetone, acetonitrile, chloroform, methylene chloride, methanol, ethanol and ethylene glycol monomethyl ether acetate. The ammonium salts according to the present invention may be readily obtained by reacting the α-ketocarboxylic acids corresponding to general formula I with the amine component at temperatures in the range of from about −20° to +50° C., preferably at room temperature, optionally in the presence of an organic solvent, such as ether, benzene, toluene, chlorobenzene, petroleum ether, acetone, dioxane, chloroform, etc. In general, approximately 1 mol of the ketocarboxylic acid is used per amine equivalent. With many diamines (for example ethylene diamine or diazabicyclooctane), it is also possible to use the salts with only one equivalent of α-ketocarboxylic acid (i.e. the mono-ammonium salts) as photo-activatable initiators according to the present invention. Accordingly, the present invention also covers polyamines of this type which are only partly neutralized with the α-ketocarboxylic acids corresponding to formula I. It is also possible by carrying out a simple preliminary test to determine how many amine nitrogen atoms of a polyamine have to be converted into the ammonium salt form in order to obtain the required deactivation.

As mentioned, the parent amines may be released at any desired time for the ammonium salts according to the present invention by photochemical decomposition under very mild conditions (temperatures as low as room temperature), i.e., by irradiation with light having a wavelength of from about 250 to 500 nm, preferably from about 300 to 400 nm.

Accordingly, the present invention also relates to a process for releasing an amine from its blocked form, characterized in that the salt of the amine with an α-ketocarboxylic acid corresponding to general formula I:

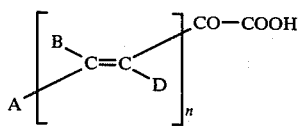

wherein A, B, D and n are defined as above, is irradiated with light having a wavelength in the range of from about 250 to 500 nm.

According to the present invention, it is possible but not necessary, to sensitize the photoreaction by the addition of triplet sensitizers known per se, such as benzophenone, acetophenone, propiophenone, xanthone, thioxanthone, etc.

The ammonium salts according to the present invention are particularly suitable for use as UV-activatable hardening catalysts for resins or resin compositions. Resins of the type in question are, for example, epoxy resins or lacquers based on isocyanates which are used either as such or in admixture with other resins.

Lacquer coatings having a crosslinked high molecular weight polyurethane structure obtained from polyhydroxyl compounds and polyisocyanates by the isocyanate-polyaddition process are already known. These commercially valuable coatings may be applied both by hand and also by machine, for example, by spray coating, dip coating or casting. In practice, they are applied either by the so-called two-component process or by the one-component process. In the two-component process, the two components (polyisocyanate on the one hand; isocyanate-reactive compound on the other hand) are mixed, optionally in the presence of a solvent. The two components can only be completely prevented from reacting by using masked polyisocyanates which only release the free isocyanate on heating. The use of systems such as these, however, is limited to stoving lacquers. Nevertheless, the lacquer mixtures containing free polyisocyanates also have a more or less long pot life which enables the lacquers to be satisfactorily applied by hand or machine to the substrates on which they subsequently harden and crosslink to form polyurethanes. In contrast, one-component systems contain an adduct with free isocyanate groups of polyhydroxyl compound and an excess of polyisocyanate, crosslinking taking place after application by reaction of the free NCO-groups in the lacquer with ater (atmospheric moisture). In this case, too, it is important to ensure that the lacquer does not undergo premature crosslinking during storage by keeping atmospheric moisture away and/or by adding water-removing agents.

On the other hand, it is desirable for the lacquer to crosslink and dry as quickly as possible after it has been applied to the substrate. Both in the case of one-component lacquers and in the case of two-component lacquers, it is possible to promote the hardening reaction by the addition of reaction accelerators known per se. The need, however, for an accelerated crosslinking reaction on the substrate conflicts with the equally important need for as long a pot life as possible. In principle, it would be possible to add a catalyst to the lacquer mixture just before it is applied to the substrate. Although this may be possible in the case of small-scale manual coating processes, it is not possible in the case of large-scale machine coating processes because the lacquer mixtures have relatively long residence times in the machine, in some cases at elevated temperature, and because an undesired reduction in the pot life by the accelerating effect of the catalyst is unavoidable. Even applying the catalyst after the lacquer mixture has been coated onto the substrate has been considered, for example, by spraying it on in gaseous form, although this requires additional elaborate machines. In addition, only a few catalysts can be processed in this way.

It is known from German Offenlegungsschrift No. 1,621,883 that a lacquer layer of a physically drying binder containing a catalyst known per se for isocyanate-polyaddition reactions can be initially applied to the surface to be lacquered, followed by the application of a catalyst-free polyurethane lacquer. In this way, it is possible to considerably shorten the drying time of a polyurethane lacquer mixture without affecting either its shelf life or its processibility. The additional expense incurred by the second lacquer coating, however, is a disadvantage.

Basically, the same problems which are encountered in the one-component and two-component polyurethane systems described above also arise in the case of coating compositions based on epoxy resins wherein the crosslinking again generally has to be catalyzed by tertiary amines. To this end, it is proposed in German Offenlegungsschrift No. 2,357,859 to add salts of tertiary amines with certain α-substituted carboxylic acids to the coating compositions. When heated to between 70° and 200° C., these ammonium salts decompose through decarboxylation, after which the coating rapidly hardens under the catalytic influence of the amine liberated. One disadvantage of this procedure is that the coating has to be heated to relatively high temperatures. This is undesirable with numerous substrates.

With the ammonium salts according to the present invention, it is now possible to obtain masked tertiary amine catalysts which enable the coating to be rapidly hardened by irradiation with short-wave light, even at temperatures as low as room temperature, and which give lacquer coatings having a particularly glossy surface.

Accordingly, the present invention also relates to coating compositions based on polyurethane or epoxide resin precursors hardening in the presence of amines, characterized in that they contain from about 0.1 to 40% by weight preferably from about 0.3 to 15% by weight, of the ammonium salts according to the invention.

The coating compositions according to the present invention may be based on the one-component and two-component polyurethane systems crosslinking in the presence of amines which are known per se in the lacquer and coating art. As briefly mentioned above, one-component systems are prepolymers, optionally dissolved in inert organic solvents, containing from about 1 to 25% by weight, preferably from about 2.5 to 19% by weight, of free NCO-groups which have been produced by reacting relatively high molecular weight and/or low molecular weight compounds containing isocyanate-reactive groups, of the type described hereinafter, with an excess of polyisocyanates of the type described hereinafter. Two component polyurethanes are a mixture, optionally dissolved in an inert organic solvent, of a relatively high molecular weight polyhydroxyl compound (including hydroxyl-containing prepolymers of polyisocyanates and an excess of polyols) on the one hand and a polyisocyanate on the other hand.

The coating compositions according to the present invention may contain aliphatic, cycloaliphatic, araliphatic, aromatic and heterocyclic polyisocyanates of the type described, for example, by W. Siefken in Justus Liebigs Annalen der Chemie, 562, pages 75 to 136, for example, those corresponding to the following general formula:

wherein
n represents about 2–4, preferably 2, and
Q represents an aliphatic hydrocarbon radical containing from about 2 to 18 carbon atoms, preferably from about 6 to 10 carbon atoms, a cycloaliphatic hydrocarbon radical containing from about 4 to 15, preferably from about 5 to 10 carbon atoms, an aromatic hydrocarbon radical containing from about 6 to 15 carbon atoms, preferably from about 6 to 13 carbon atoms, or an araliphatic hydrocarbon radical containing from about 8 to 15 carbon atoms, preferably from about 8 to 13 carbon atoms. Examples are as follows: ethylene diisocyanate, 1,4-tetramethylene diisocyanate, 1,6-hexamethylene diisocyanate, trimethyl hexamethylene diisocyanate, 1,12-dodecane diisocyanate, cyclobutane-1, 3-diisocyanate, cyclohexane-1,3- and 1,4-diisocyanate and mixtures of these isomers, 1-isocyanato-3, 3,5-trimethyl5-isocyanatomethyl cyclohexane (German Auslegeschrift No. 1,202,785, U.S. Pat. No. 3,401,190), 2,4-and 2,6-hexahydrotolylene diisocyanate and mixtures of these isomers, hexahydro-1,3- and/or -1,4-phenylene diisocyanate, perhydro-2,4'- and/or -4,4'-diphenyl methane diisocyanate, 1, 3- and 1,4-phenylene diisocyanate, 2,4- and 2,6-tolylene diisocyanate and mixtures of these isomers, diphenyl methane -2,4'- and/or -4,4'-diisocyanate, and naphthylene-1,5-diisocyanate.

According to the present invention, it is also possible, for example, to use triphenyl methane-4,4'-triisocyanate, polyphenyl polymethylene polyisocyanates of the type obtained by condensing aniline with formaldehyde, followed by phosgenation, and described, for example, in British Pat. Nos. 874,430 and 848,671, m- and p-isocyanatophenyl sulphonyl isocyanates according to U.S. Pat. No. 3,454,606, perchlorinated aryl polyisocyanates of the type described, for example, in German Auslegeschrift No. 1,157,601 (U.S. Pat. No. 3,277,138), polyisocyanates containing carbodiimide groups of the type described in German Pat. No. 1,092,007 (U.S. Pat. No. 3,152,162) and in German Offenlegungsschrift Nos. 2,504,400, 2,537,685 and 2,552,350, norbornane diisocyanates according to U.S. Pat. No. 3,492,330, polyisocyanates containing allophanate groups of the type described, for example, in British Pat. No. 994,890, in Belgian Pat. No. 761,626 and in Dutch Patent Application No. 7,102,524, polyisocyanates containing isocyanurate groups of the type described, for example, in U.S. Pat. No. 3,001,973, in German Pat. Nos. 1,022,789; 1,222,067 and 1,027,394 and in German Offenlegungsschrift Nos. 1,929,034 and 2,004,048, polyisocyanates containing urethane groups of the type described, for example, in Belgian Pat. No. 752,261 or in U.S. Pat. Nos. 3,394,164 and 3,644,457, polyisocyanates containing acylated urea groups according to German Pat. No. 1,230,778, polyisocyanates containing biuret groups of the type described, for example, in U.S. Pat. Nos. 3,124,605; 3,201,372 and 3,124,605 and in British Pat. No. 889,050, polyisocyanates produced by telomerization reactions of the type described, for example, in U.S. Pat. No. 3,654,106, polyisocyanates containing ester groups of the type described, for example, in British Pat. Nos. 965,474 and 1,072,956, in U.S. Pat. No. 3,567,763 and in German Pat. No. 1,231,688, reaction products of the above-mentioned diisocyanates with acetals according to German Pat. No. 1,072,385 and polyisocyanates containing polymeric fatty acid esters according to U.S. Pat. No. 3,455,883.

It is also possible to use the isocyanate-group-containing distillation residues obtained in the commercial production of isocyanates, optionally in solution in one or more of the above-mentioned polyisocyanates. It is also possible to use any mixtures of the above-mentioned polyisocyanates.

Preferred polyisocyanates are hexamethylene diisocyanate, its isocyanurate and its biuret; 1-isocyanato3,3,5-trimethyl-5-isocyanatomethyl cyclohexane (isophorone diisocyanate); the tolylene diisocyanates and their isocyanurates; the mixed isocyanurate of tolylene diisocyanate and hexamethylene diisocyanate;

the reaction product of 1 mol of trimethylol propane and 3 mols of tolylene diisocyanate and also crude diphenyl methane diisocyanate.

Suitable relatively high molecular weight compounds containing at least 2 isocyanate-reactive hydrogen atoms are those having a molecular weight of generally from about 400 to 50,000. In addition to compounds containing amino groups, thiol groups or carboxyl groups, compounds such as these are preferably compounds containing hydroxyl groups, particularly compounds containing from about 2 to 8 hydroxyl groups and, above all, compounds having a molecular weight of from about 500 to 25,000, preferably from about 700 to 20,000, for example, polyesters, polyethers, polythioethers, polyacetals, polycarbonates and polyester amides containing at least 2, generally from about 2 to 8, but preferably from about 2 to 4 hydroxyl groups, or even OH-prepolymers of these compounds and a less than equivalent quantity of polyisocyanate, of the type known per se for the production of homogeneous and cellular polyurethanes.

(a) The polyesters containing hydroxyl groups suitable for use in accordance with the present invention are, for example, reaction products of polyhydric, preferably dihydric and, optionally, trihydric alcohols with polybase, preferably dibasic, carboxylic acids. Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic and/or heterocyclic and may optionally be substituted, for example, by halogen atoms, and/or unsaturated.

Examples of carboxylic acids such as these and their derivatives are succinic acid, adipic acid, suberic acid, azelaic acid, sebacic acid phthalic acid, isophthalic acid, terephthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, furmaric acid, dimerized and trimerized unsaturated fatty acids, optionally in admixture with monomeric unsaturated fatty acids, such as oleic acid, terephthalic acid dimethyl ester and terephthalic acid-bis-glycol ester. Suitable polyhydric alcohols are, for example, ethylene glycol, 1,2- and 1,3-propylene glycol, 1,4- and 2,3-butylene glycol, 1,6-hexane diol, 1,8-octane diol, neopentyl glycol, 1,4-bis-hydroxymethyl cyclohexane, 2-methyl-1,3- propane diol, glycerol, trimethylol propane, 1,2,6-hexane triol, 1,2,4-butane triol, trimethylol ethane, pentaerythritol, quinitol, mannitol, sorbitol, formitol, methyl glycoside, also diethylene glycol, triethylene glycol, tetraethylene glycol and higher polyethylene glycols, dipropylene glycol and higher polypropylene glycols, dibutyl glocol and higher polybutylene glycols. The polyesters may contain terminal carboxyl groups. Polyesters of lactones, for example, $\epsilon$-caprolactone, or of hydroxy carboxylic acids, for example, $\omega$-hydroxy caproic acid, may also be used.

(b) The polyethers containing at least 2, generally about 2 to 8 and preferably about 2 or 3 hydroxyl groups suitable for use in accordance with the present invention are also known per se and are obtained, for example, by polymerizing epoxides, such as ethylene oxide, propylene oxide, butylene oxide, tetrahydrofuran, styrene oxide or epichlorhydrin on their own, for example, in the presence of Lewis catalysts, such as $BF_3$, or by the addition of these epoxides, preferably ethylene oxide or propylene oxide, optionally in admixture or successively, with starter components containing reactive hydrogen atoms, such as water, alcohols, ammonia or amines, for example, ethylene glycol, 1,3-propylene glycol or 1,2-propylene glycol, trimethylol propane, glycerol, sorbitol, 4,4'-dihydroxy diphenyl propane, aniline, ethanolamine or ethylene diamine. Sucrose polyethers of the type described, for example, in German Auslegeschrift Nos. 1,176,358 and 1,064,938 and formitol- or formose-started polyethers (German Offenlegungsschrift Nos. 2,639,083 and 2,737,951) may also be used in accordance with the present invention. In many cases, it is preferred to use polyethers which predominantly contain primary OH-groups (up to about 90% by weight, based on all the OH-groups present in the polyether). Polybutadienes containing OH-groups are also suitable for use in accordance with the present invention.

(c) Among the polythioethers, reference is made in particular to the condensation products of thiodiglycol on its own and/or with other glycols, dicarboxylic acids, formaldehyde, aminocarboxylic acids or amino alcohols. Depending on the co-components, the products in question are, for example, polythio mixed ethers, polythioether esters or polythioether ester amides.

(d) Suitable polyacetals are, for example, the compounds obtainable from glycols, such as diethylene glycol, triethylene glycol, 4,4'-dioxethoxy diphenyl dimethyl methane, hexane diol and formaldehyde. Polyacetals suitable for use in accordance with the present invention may also be obtained by polymerizing cyclic acetals such as trioxane (German Offenlegungsschrift No. 1,694,128).

(e) Suitable polycarbonates containing hydroxyl groups are known per se and can be obtained, for example, by reacting diols, such as 1,3-propane diol, 1,4-butane diol and/or 1,6-hexane diol, diethylene glycol, triethylene glycol, tetraethylene glycol or thiodiglycol, with diaryl carbonates, for example, diphenyl carbonates, or phosgene (German Auslegeschrift Nos. 1,694,080, 1,915,908 and 2,221,751; German Offenlegungsschrift No. 2,605,024).

(f) The polyester amides and polyamides include, for example, the predominantly linear condensates obtained, for example, from polybasic saturated or unsaturated carboxylic acids or their anhydrides and polyhydric saturated or unsaturated amino alcohols, diamines, polyamines and mixtures thereof.

(g) Polyhydroxyl compounds already containing urethane or urea groups and optionally modified natural polyols, such as castor oil or carbohydrates, for example, starch, may also be used. Addition products of alkylene oxides with phenol/formaldehyde resins or even with urea/formaldehyde resins may also be used in accordance with the present invention.

(h) Before they are used in the polyisocyanate-polyaddition process, the above-mentioned polyhydroxyl compounds may be modified in various ways. Thus, according to German Offenlegungsschrift Nos. 2,210,839 (U.S. Pat. No. 3,849,515) and 2,544,195, a mixture of different polyhydroxyl compounds (for example, a polyether polyol and a polyester polyol) may be condensed by etherification in the presence of a strong acid to form a relatively high molecular weight polyol which is made up of different segments attached through ether bridges.

(i) According to the present invention, it is also possible to use polyhydroxyl compounds containing high molecular weight polyadducts and polycondensates or polymers in a finely dispersed or dissolved form. Polyhydroxyl compounds such as these are obtained, for example, by carrying out polyaddition reactions (for example, reactions between polyisocyanates and aminofunctional compounds) and polycondensation reactions (for example, between formaldehyde and phenols and/or amines) in situ in the above-mentioned compounds containing hydroxyl groups. Processes such as these are described, for example, in German Auslegeschrift Nos. 1,168,075 and 1,260,142 and in German Offenlegungsschrift Nos. 2,324,134; 2,423,984; 2,512,385; 2,513,815, 2,550,796 2,550,797; 2,550,833; 2,550,862; 2,633,293 and 2,639,254. It is also possible, however, in accordance with U.S. Pat. No. 3,869,413 or German Offenlegungsschrift No. 2,550,860, to mix an aqueous polymer dispersion with a polyhydroxyl compound and subsequently to remove the water from the mixture.

Polyhydroxyl compounds modified by vinyl polymers of the type obtained, for example, by polymerizing styrene and acrylonitrile in the presence of polyethers (U.S. Pat. Nos. 3,383,351; 3,304,273; 3,523,093 and 3,110,695; German Auslegeschrift No. 1,152,536) or polycarbonate polyols (German Patent No. 1,769,795; U.S. Pat. No. 3,637,909) are also suitable for use in the process according to the present invention. Plastics having particularly good flameproof properties are obtained by using polyether polyols modified in accordance with German Offenlegungsschrift Nos. 2,442,101; 2,644,922 and 2,646,141 by graft polymerization with vinyl phosphonic acid esters and, optionally, (meth) acrylonitrile, (meth)acrylamide or OH-functional (meth)acrylic acid esters. Polyhydroxyl compounds into which carboxyl groups have been introduced by radical graft polymerization with unsaturated carboxylic acids and, optionally, other olefinically unsaturated monomers (German Offenlegungsschrift Nos. 2,714,291; 2,739,620 and 2,654,746) particularly may be advantageously used in combination with mineral fillers.

Where modified polyhydroxyl compounds of the type mentioned above are used as starting components in the polyisocyanate-polyaddition process, polyurethanes having considerably improved mechanical properties are formed in many cases.

Representatives of the above-mentioned compounds used in accordance with the present invention are described, for example, in High Polymers, Vol. XVI, "Polyurethanes, Chemistry and Technology", by Saunders-Frisch, Interscience Publishers, New York/London, Vol. I, 1962, pages 32 to 42 and pages 44 to 54 and Vol. II, 1964, pages 5-6 and 198-199, and in Kunststoff-Handbuch, Vol. VII, Vieweg-Hochtlen, Carl-Hanser-Verlag, Munich, 1966, for example, on pages 45 to 71. It is, of course, possible to use mixtures of the above-mentioned compounds containing at least two isocyanate-reactive hydrogen atoms and having a molecular weight of from about 400 to 50,000, for example, mixtures of polyethers and polyesters.

In some cases, it is particularly advantageous to combine low-melting and high-melting polyhydroxyl compounds with one another (German Offenlegungsschrift No. 2,706,297).

Low molecular weight compounds containing at least two isocyanate-reactive hydrogen atoms (molecular weight from about 32 to 400) suitable for use in accordance with the present invention are, once again compounds preferably containing hydroxyl groups and generally containing from about 2 to 8, preferably from about 2 to 4 isocyanate-reactive hydrogen atoms.

In this case, too, it is possible to use mixtures of different compounds containing at least two isocyanatereactive hydrogen atoms and having a molecular weight in the range of from about 32 to 400.

Examples of compounds such as these are ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis-hydroxymethyl cyclohexane, 2-methyl-1,3- propane diol, dibromobutene diol (U.S. Pat. No. 3,723,392), glycerol, trimethylol propane, 1,2,6-hexane triol, trimethylol ethane, pentaerythritol, quinitol, mannitol, sorbitol, castor oil, diethylene glycol, triethylene glycol, tetraethylene glycol, higher polyethylene glycols having a molecular weight of up to about 400, dipropylene glycol, higher polypropylene glycols having a molecular weight of up to about 400, dibutylene glycol, higher polybutylene glycols having a molecular weight of up to about 400, 4,4'-dihydroxy diphenyl propane and dihydroxy methyl hydroquinone.

Other low molecular weight polyols suitable for the purposes of the present invention are the mixtures of hydroxy aldehydes and hydroxy ketones ("formose") of the polyhydric alcohols obtained therefrom by reduction ("formitol") which are formed in the autocondensation of formaldehyde hydrate in the presence of metal compounds as catalysts and compounds capable of enediol formation as co-catalysts (German Offenlegungsschrift Nos. 2,639,084; 2,714,084; 2,714,104; 2,721,186; 2,738,154 and 2,738,512). Solutions of polyisocyanate polyaddition products, particularly solutions of polyurethane ureas containing ionic groups and/or solutions of polyhydrazodicarbonamides, in low molecular weight polyhydric alcohols may also be used as the polyol component in accordance with the present invention (German Offenlegungsschrift No. 2,639,759).

Coating systems based on epoxy resin precursors suitable for use in accordance with the present invention are, for example, triglycidyl isocyanurate; polyepoxides having a molecular weight of up to about 2000 of the type obtained from bisphenol A and epichlorohydrin; bisglycidyl esters of terephthalic acid, isophthalic acid, phthalic acid, tetrahydrophthalic acid, hexahydrophthalic acid or hexahydroterephthalic acid; triglycidyl esters of trimellitic acid; tetraglycidyl esters and β-methyl glycidyl esters of pyromellitic acid; glycidly derivatives of hydantoin corresponding to the following general formula:

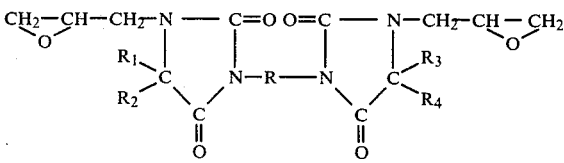

wherein
R represents a difunctional aliphatic, cycloaliphatic or aralphatic radical and
$R_1$, $R_2$, $R_3$, and $R_4$ each represent a hydrogen atom or an aliphatic or cycloaliphatic hydrocarbon radical, or $R_1$ and $R_2$ or $R_3$ and $R_4$ together represent a difunctional aliphatic or cycloaliphatic hydrocarbon radical, preferably a tetramethylene or pentamethylene radical. In the above general formula, $R_1$, $R_2$, $R_3$ and $R_4$ preferably represent hydrogen or a lower alkyl radical containing from about 1 to 4 carbon atoms while R preferably represents an alkylene radical containing from 1 to 4 carbon atoms.

Other polyepoxide resins suitable for the purposes of the present invention may be obtained by condensing epichlorhydrin with primary and/or secondary amines, polyesters containing hydroxyl and/or carboxyl groups, phenol/formaldehyde condensates containing hydroxyl groups or even polyether polyols. These polyepoxide resins are hardened by a known method with amines or polyamines, amides or polyamides, polycarboxylic acids (including polyesters containing free carboxyl groups) or even with compounds containing mercapto groups or phenolic hydroxyl groups.

Other resins, such as ketone resins, nitrocellulose, PVC copolymers, cellulose acetobutyrates etc., may, of course, also be added to the lacquer systems according to the present invention in order to obtain particular properties. Other auxiliaries of the type commonly used in the lacquer art, such as levelling aids, pigments, fillers and other additives known per se, may also be used.

The coating compositions according to the present invention may contain up to about 90% by weight and preferably up to about 60% by weight of an organic solvent. Examples of suitable organic solvents are toluene, xylene, non-aromatic and substantially non-aromatic hydrocarbon fractions, ethylacetate, butylacetate, ethylene glycol monomethyl ether acetate, ethylene glycol monoethyl ether acetate, acetone, methylethyl ketone, cyclohexanone and mixtures of these compounds.

The coating compositions according to the present invention are suitable for lacquering and coating all kinds of substrates, for example, metals, such as aluminum or steel, asbestos cement, leather, textiles, rubber, paper, glass, stone and a variety of different plastics. They are particularly suitable for lacquering wood and metal.

The lacquer and coating systems according to the present invention are preferably processed by machine. They are applied by techniques known per se such as extrusion coating, spray coating, dip coating, roll coating and casting. The layer thicknesses are generally between about 1 and 1000μ, preferably between about 4 and 200μ.

After the lacquer or coating has been applied, it is irradiated with light having a wavelength of from about 250 to 500 nm. The irradiation time is generally between about 0.1 and 300 seconds and preferably between about 1 and 80 seconds, depending on the thickness of the layer applied and the power of the light source. As already explained, the ammonium salt according to the present invention which is present in the lacquer decomposes through decarboxylation under the influence of short-wave light. The amine released then acts as a catalyst for the hardening reaction or, in the case of the amonium salt of a primary or secondary polyamide, in known manner as a crosslinking agent, for example, for a prepolymer containing free NCO-groups.

According to the present invention, coating is preferably carried out at about room temperature (from approximately 10° to 30° C.). Since the ammonium salts according to the present invention also undergo thermal decomposition on heating, the hardening reaction may be further accelerated by heating (up to about 130° C., preferably up to about 90° C.). The advantage of the resin composition according to the present invention, however, lies in the fact that they may also be processed at low temperatures, i.e., without any thermal stressing of the substrate.

The coating compositions according to the present invention have a surprisingly long shelf life, i.e., a long pot life, at room temperature. When irradiated with shortwave light, however, they gel extremely quickly and then harden quickly, surprisingly even when the coating systems in question are pigmented systems and not clear lacquers.

The invention is illustrated by the following Examples in which the quantities quoted represent parts by weight or percentages by weight, unless otherwise indicated.

EXAMPLE 1

A Solution of 5.5 g of diazabicyclooctane (DABCO®) in 100 ml of ether is added dropwise to a solution of 9.5 g of p-methyl benzylidene pyruvic acid in 200 ml of ether. The mono-ammonium salt of the diazabicyclooctane is quantitatively obtained in crystalline form. M.p.: 188°–191° C.

Further examples of ammonium salts of benzylidene pyruvic acids corresponding to the following general formula:

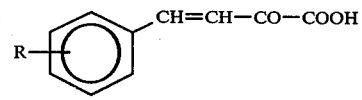

are shown in the following Table. The literature references given relate to the free acids.

TABLE

| Example No. | R | Acid Amine | Method | Yield (%) | M.p (°C.) | Literature* |
|---|---|---|---|---|---|---|
| 2 | H | DABCO® | I | 50 | 59–61 | (1) |
| 3 | 4-Cl | " | II | 58 | 138–139 | (4) |
| 4 | 4-CF$_3$ | " | II | 27 | 106–108 | |
| 5 | 4-OCH$_3$ | triethylamine | II | 93 | 129–130 | (3) |
| 6 | 4-NO$_2$ | DABCO® | II | 31 | 195–197 | (5) |
| 7 | 4-CN | " | II | 15 | 185 (decomp) | |
| 8 | 2-Cl | " | I | 66 | 99–102 | |
| 9 | 2-OCH$_3$ | " | I | 31 | 132–134 | (2) |
| 10 | 3-NO$_2$ | " | III | 40 | 147–148 | (6,5) |
| 11 | 3-Cl | " | II | 47 | 78–80 | |
| 12 | 2,6-Cl | " | II | 70 | 152–153 | |

| Example No. | Salt M.p (°C.) | Yield (%) |
|---|---|---|
| 2 | 140–153 | 95 |
| 3 | 188 (decomp.) | 97 |
| 4 | 178 (decomp.) | 92 |
| 5 |  | 93 |
| 6 | 197 (decomp.) | 100 |
| 7 | 187 (decomp.) | 87 |
| 8 | 120 (decomp.) | 87 |
| 9 | 141–152 | 90 |
| 10 | 189 (decomp.) | 100 |
| 11 | 128–142 | 97 |

TABLE-continued

| 12 | 148–158 | 100 |

*(1) M. Reimer, J. Am. Chem. Soc. 46, 783 (1924)
(2) M. Reimer et. al., Chem. Soc. 60, 2469 (1938)
(3) M. Reimer et. al., Chem. Soc. 50, 2506 (1928)
(4) E. D. Stecher et. al., J. Org. Chem. 38, 4453 (1973)
(5) E. A. Ibrahim et. al., Pharmazie 27, 731 (1972)
(6) E. D. Stecher et. al., J. Org. Chem. 30, 1800 (1965)

PRODUCTION OF THE BENZYLIDENE PYRUVIC ACIDS

Method I 42.4 g (0.4 mol) of benzaldehyde or 0.4 mol of the substituted benzaldehyde are added dropwise at 0° C. to a solution of 35.2 g (0.4 mol) of pyruvic acid in 160 ml of 10% NaOH, followed by the dropwise addition of another 80 ml of 10% NaOH. After stirring for several hours at room temperature, the salt precipitated is filtered off under suction, washed with cold methanol and ether and then dissolved in water. After acidification using hydrochloric acid, the benzylidene pyruvic acid precipitates in crystalline form. The crystals are filtered off under suction, dissolved in ether and the ethereal solution is dried with $Na_2SO_4$. After the solvent has been evaporated off, the acid is recrystallized from benzene.

Method II

A mixture of 35.2 g (0.4 mol) of pyruvic acid and 0.4 mol of the substituted benzaldehyde is added dropwise at 80° C. to 110 ml of a 25% solution of KOH in methanol. The mixture is then left standing for 18 hours at room temperature. The salt precipitated is then filtered off under suction, washed with methanol and ether, dissolved in water and acidified. The crystalline acid precipitating is filtered off after suction, dissolved in ether and dried. After the solvent has been distilled off, the acid is recrystallized from benzene.

Method III

A solution of 17.6 g (0.2 mol) of pyruvic acid and 30.2 g (0.2 mol) of m-nitrobenzaldehyde in 240 ml of methanol is heated for 90 minutes to 70° C. with a solution of 22 g of $Na_2CO_3$ in 240 ml of water. After the solution has cooled to 0° C., the salt precipitates and is filtered off under suction and washed with ether. Dissolution in water and acidification give the required acid in a yield of 40%.

EXAMPLE 13

A solution of 1 g of DABCO in 50 ml of ether is added dropwise to a solution of 2 g of 6-phenyl-2-oxohexadiene-3,5-carboxylic acid in 20 ml of ether. The DABCO salt is obtained in crystalline form in a yield of 2.8 g, 93% of the theoretical yield.

EXAMPLE 14

Coating compositions are produced by mixing 264 parts of a polyol component A, 100 parts of a polyisocyanate component B and (a) 5 parts of triethyl ammonium salt of p-methyl benzylidene pyruvic acid or
(b) 5 parts of the dimethyl benzyl ammonium salt of p-methyl benzylidene pyruvic acid.

Even after storage for 7 hours at room temperature both lacquers (a) and (b) are still processable.

The coating compositions are applied to degreased glass plates in a layer thickness of 60μ. After airing for 30 minutes, the plates are placed at a distance of 6 cm below a U-lamp of the Hanau Q 500 type maximum intensity at around 300 to 320 nm) and irradiated for 60 seconds. After hardening for 24 hours at room temperature, the coatings are very hard (pencil hardness according to the ECCD standard of the European Coil Coating Association).

Polyol component A is a mixture of 100 parts of a titanium dioxide (rutile) pigment and 164 parts of a 61% solution of a polyester of 3 mols of phthalic acid anhydride, 3.5 mols of trimethylol propane and 0.05 mol of maleic acid anhydride (8% of OH-groups; acid number=4) in ethylene glycol monoethyl ether acetate.

Polyisocyanate B is a 75% solution of a poly-functional biuret polyisocyanate of 3 mols of hexamethylene diisocyanate and 1 mol of water in ethylene glycol monoethyl ether acetate:xylene (1:1).

EXAMPLE 15 (Comparison)

The procedure is as described in Example 14, except that 5 parts of endoethylene piperazine are used instead of the ammonium salts. After storage for only 3 hours at room temperature, the coating composition has gelled and can no longer be processed.

EXAMPLE 16 (Comparison)

The procedure is as described in Example 14 except that the ammonium salt is not added. The coatings are still very soft (pencil hardness: B to HB) after storage for 24 hours at room temperature.

It is to be understood that any of the components and conditions mentioned as suitable herein can be substituted for it counterpart in the foregoing examples and that although the invention has been described in considerable detail in the foregoing, such detail is solely for the purpose of illustration. Variation can be made in the invention by those skilled in the art without departing from the spirit and scope of the invention except as is set forth in the claims.

What is claimed is:

1. Ammonium salts of α-ketocarboxylic acids corresponding to the following general formula:

$$\left[ \begin{array}{c} B \\ A \end{array} C=C \begin{array}{c} CO-COOH \\ D \end{array} \right]_n$$

wherein n represents an integer of from about 1 to 4

A and B are the same or different and represent hydrogen, an optionally branched and/or halogen- or methoxy-substituted $C_1$–$C_{10}$-alkyl radical, a $C_5$–$C_{15}$-cycloalkyl radical, a $C_6$–$C_{15}$-aryl radical which may optionally be substituted by —OH, —R, —OR, —SR, halogen, —$NO_2$, —COR, —COOH, —CN, —COOR, —$CONH_2$, —OR', —SR' or —COR', a $C_4$–$C_{10}$-heterocyclic radical containing oxygen, sulphur and/or nitrogen as a hetero atom or A and B together represent a 5-membered or 6-membered cycloaliphatic ring optionally containing oxygen or nitrogen as a hetero atom, and D represents hydrogen, halogen, —OH, —COOH, —COOR, CN, —COOH, —OR, —COR, —COR', —CCl$_3$, an optionally branched C$_1$–C$_{10}$-alkyl radical, a C$_4$–C$_{15}$-cycloalkyl radical, a C$_6$–C$_{15}$-aryl radical which may optionally be substituted by —OH, —R, —OR, —SR, halogen, —NO$_2$, —COR, —COOH, —CN, —COOR, —CONH$_2$, —OR', —SR', or —COR' or a C$_4$–C$_{10}$-heterocyclic radical containing oxygen and/or nitrogen as a hetero atom, wherein R represents an optionally halogen-substituted alkyl group containing from about 1 to 6 carbon atoms and R' represents an aryl group containing from about 6 to 12 carbon atoms.

2. The ammonium salts of claim 1, wherein n is 1 or 2.

3. The ammonium salts of claim 1, wherein D and A or B is hydrogen.

4. The ammonium salts of claim 1, wherein A or B is an aryl radical.

5. The ammonium salts of claim 1, wherein the amine component has a molecular weight of from about 31 to 500.

6. The ammonium salts of claim 1, wherein the amine component has a molecular weight of from about 100 to 300.

7. The ammonium salts of claim 1, wherein the amine component contains from about 1 to 3 amine nitrogen atoms.

8. The ammonium salts of claim 1, wherein the amine component is a tertiary amine.

9. A process for releasing an amine from its blocked form, characterized in that the ammonium salt of claim 1 is irradiated with light having a wavelength of from about 250 to 500 nm.

10. Coating compositions based on polyurethane or epoxide precursors hardening in the presence of amines, characterized in that they contain from about 0.1 to 40% by weight, based on the solids content, of the ammonium salts of claim 1.

11. A process for producing ammonium salts of α-ketocarboxylic acids corresponding to the following general formula:

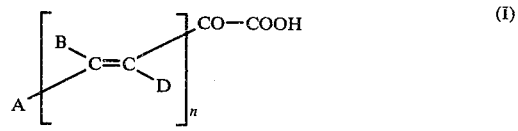

wherein n represents an integer of from about 1 to 4,

A and B are the same or different and represent hydrogen, an optionally branched and/or halogen- or methoxy-substituted C$_1$–C$_{10}$-alkyl radical, a C$_5$–C$_{15}$-cycloalkyl radical, a C$_6$–C$_{15}$-aryl radical which may optionally be substituted by —OH, —R, —OR, —SR, halogen, —NO$_2$, —COR, —COOH, —CN, COOR, —CONH$_2$, —OR', —SR' or —COR', a C$_4$–C$_{10}$-heterocyclic radical containing oxygen, sulphur and/or nitrogen as a hetero atom or A and B together represent a 5- membered or 6-membered cycloaliphatic ring optionally containing oxygen or nitrogen as a hetero atom, and D represents hydrogen, halogen, —OH, —COOH, —COOR, —CH, —COOH, —OR, —COR, —COR', —CCL$_3$, an optionally branched C$_1$–C$_{10}$-alkyl radical, a C$_4$–C$_{15}$-cycloalkyl radical, a C$_6$–C$_{15}$-aryl radical which may optionally be substituted by —OH, —R, —OR, —SR, halogen, —NO$_2$, —COR, —COOH, —CN, —COOR, —CONH$_2$, OR', —SR', or —COR' or a C$_4$–C$_{10}$-heterocyclic radical containing oxygen and/or nitrogen as a hetero atom, wherein R represents an optionally halogen-substituted alkyl group containing from about 1 to 6 carbon atoms and R' represents an aryl group containing from about 6 to 12 carbon atoms comprising reacting α-ketocarboxylic acids of the formula I with an amine component having a molecular weight between about 31 to 500 at temperatures in the range of from about −20° to +50° C.

12. In a process for coating substrates with coating compositions based on polyurethane or epoxide precursors which harden in the presence of amines, the improvement wherein said compositions contain from about 0.1 to 40% by weight, based on the solids content, of ammonium salts of α-ketocarboxylic acids corresponding to the following general formula:

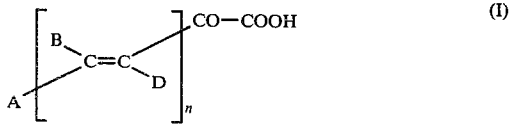

wherein n represents an integer of from about 1 to 4,

A and B are the same or different and represent hydrogen, an optionally branched and/or halogen- or methoxy-substituted C$_1$–C$_{10}$-alkyl radical, a C$_5$–C$_{15}$-cycloalkyl radical a C$_6$–C$_{15}$-aryl radical which may optionally be substituted by —OH, —R, —OR, —SR, halogen, —NO$_2$, —COR, —COOH, —CN, COOR, —CONH$_2$, —OR', —SR' or —COR', a C$_4$–C$_{10}$-heterocyclic radical containing oxygen, sulphur and/or nitrogen as a hetero atom or A and B together represent a 5-membered or 6 membered cycloaliphatic ring optionally containing oxygen or nitrogen as a hetero atom, and D represents hydrogen, halogen, —OH, —COOH, —COOR, —CH, —COOH, —OR, —COR, —COR', —CCl$_3$, an optionally branched C$_1$–C$_{10}$-alkyl radical, a C$_4$–C$_{15}$-cycloalkyl radical, a C$_6$–C$_{15}$-aryl radical which may optionally be substituted by —OH, —R, —OR, —SR, halogen, —NO$_2$, —COR, —COOH, —CN, —COOR, —CONH$_2$, —OR', —SR', or —COR' or a C$_4$–C$_{10}$-heterocyclic radical containing oxygen and/or nitrogen as a hetero atom, wherein R represents an optionally halogen-substituted alkyl group containing from about 1 to 6 carbon atoms and R' represents an aryl group containing from about 6 to 12 carbon atoms and said composition is irradiated with light having a wavelength of from about 250 to 500 nm.

* * * * *